United States Patent
Kim et al.

[11] Patent Number: 6,124,503
[45] Date of Patent: Sep. 26, 2000

[54] PROCESSES FOR MAKING AND USING ALKYLAMINOARYLCARBONYL COMPOUNDS

[75] Inventors: Chang-Kyu Kim, Pittsford; Jared B. Mooberry; David Hoke, both of Rochester; James J. Seifert, Hilton, all of N.Y.

[73] Assignee: Eastman Kodak Company, Rochester, N.Y.

[21] Appl. No.: 09/223,863

[22] Filed: Dec. 31, 1998

[51] Int. Cl.[7] .................................................. C07C 211/03
[52] U.S. Cl. ........................................... 564/305; 564/431
[58] Field of Search ..................................... 564/431, 305

[56] References Cited

U.S. PATENT DOCUMENTS

| | | | |
|---|---|---|---|
| 4,840,884 | 6/1989 | Mooberry et al. | 430/557 |
| 5,457,004 | 10/1995 | Mooberry et al. | 430/226 |

*Primary Examiner*—Joseph McKane
*Attorney, Agent, or Firm*—Arthur E. Kluegel

[57] ABSTRACT

A method of making an alkylaminoarylcarbonyl compound having Formula I:

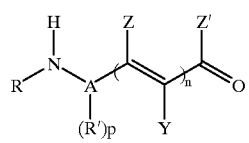

Formula I wherein
- R is an alkyl group;
- A is an aryl (including heteroaryl) ring;
- each R' is independently an alkyl group which may form a ring with Z or Z';
- p is 0, 1, 2, or 3;
- each Z, Z', and Y is independently hydrogen or a substituent; and
- n is 0, 1, or 2;

comprising:
(a) blocking the carbonyl function of an aminoarylcarbonyl compound via condensation with an active methylene compound
(b) alkylating this blocked amniocarbonyl compound via reductive alkylation with an alkyl or aryl (including heteroaryl) carbonyl compound, and
(c) deblocking of the blocked alkylaminoarylcarbonyl compound via base hydrolysis to regenerate the carbonyl function and give the desired alkylaminocarbonyl compound.

16 Claims, No Drawings

PROCESSES FOR MAKING AND USING ALKYLAMINOARYLCARBONYL COMPOUNDS

FIELD OF THE INVENTION

This invention relates to a method of making a certain alkylaminoarylcarbonyl compound using blocking, alkylating and deblocking steps and a method of using the compound so made.

BACKGROUND OF THE INVENTION

It has been known to employ a releasable dye as the coupling-off group to provide a so-called 'high dye-yield' coupler. Such a coupler reacts with oxidized color developer to form one dye and in doing so releases a second dye. The net result is the formation of two molecules of dye with 2-equivalents of silver. It enables one to reduce the amount of coupler, silver, and other materials to be included in the film layers. It also enables thinner layers which in turn reduce the amount of light scatter to improve sharpness in underlying layers. Thinner layers can also reduce the level of unwanted absorption which can further enhance the image quality in underlying layers. The benefits of the high dye-yield couplers are thus particularly advantageous in the uppermost layers, i.e., in the blue sensitive layers, in conventional color negative layer arrangements.

The first useful high dye-yield couplers have been disclosed by J. Mooberry and S. Singer in U.S. Pat. No. 4,840,884. J. Mooberry, et. al. have later disclosed improved high dye-yield couplers with methine dye chromophore in U.S. Pat. No. 5,457,004. The latter patent teaches a few advantages of using the methine dyes. Compared to couplers releasing analogous azo dyes, the couplers releasing methine dyes provide much higher extinction and superior photographic properties such as hue and dispersibility.

One of the obstacles in commercializing high dye-yield couplers is difficulty of synthesis. The complex molecule requires a number of synthetic steps some of which are too difficult to adapt in a large scale manufacturing. In the J. Mooberry, et al. patent a method has been described for synthesis of a high dye-yield yellow coupler. It requires a large number of synthetic steps and the yield of product is less than desired.

U.S. Pat. No. 5,457,004 discloses the use of alkylaminoarylcarbonyl intermediate compounds. A method for the synthesis of the high dye-yield coupler relies on such an intermediate to begin the preparation of the coupler. It is therefore a problem to be solved to provide a general method of making and using alkylaminoarylcarbonyl compounds which serve as the starting materials or intermediates.

SUMMARY OF THE INVENTION

The invention provides a method of making an alkylaminoarylcarbonyl compound having Formula I:

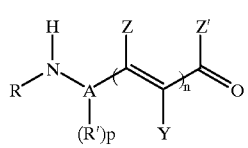

Formula I wherein
R is an alkyl group;
A is an aryl (including heteroaryl) ring;

each R' is independently an alkyl group which may form a ring with Z or Z';
p is 0, 1, 2, or 3;
each Z, Z', and Y is independently hydrogen or a substituent; and
n is 0, 1, or 2;
comprising:
(a) blocking the carbonyl function of an aminoarylcarbonyl compound of the formula:

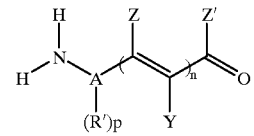

via condensation with an active methylene compound of formula:

wherein
each E' and E" is independently an electron withdrawing group; whereby there results a blocked aminoarylcarbonyl compound of formula:

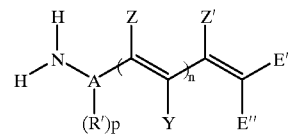

(b) alkylating this blocked amniocarbonyl compound via reductive alkylation with an alkyl or aryl (including heteroaryl) carbonyl compound to give a blocked alkylaminoarylcarbonyl compound of formula:

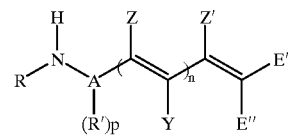

(c) deblocking of the blocked alkylaminoarylcarbonyl compound via base hydrolysis to regenerate the carbonyl function and give the desired alkylaminocarbonyl compound.

In another aspect this invention relates to alkylaminoarylcarbonyl compounds, inter-mediates for the preparation of high dye-yield couplers, the intermediates having the following structural formula:

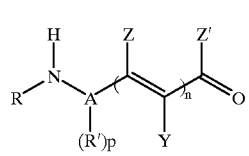

Formula I wherein

R is a substituted or unsubstituted alkyl group;

A is a substituted or unsubstituted aryl (including heteroaryl) ring;

each R' is independently a substituted or unsubstituted alkyl group which may form a ring with Z or Z';

p is 0, 1, 2, or 3;

each Z, Z', and Y is independently hydrogen or a substituent; and n is 0, 1, or 2.

In yet another aspect this invention relates to a method of using the intermediates of Formula I made by the foregoing method in the preparation of high dye yield couplers, the method comprising the steps of:

(1) making a carbamyl (or thiocarbamyl) chloride of alkylaminoarylcarbonyl compound of Formula I with phosgene (or thiophosgene);

(2) reacting it with a coupler-timing group piece to form a carbamyl (or thiocarbamyl) link between the coupler-timing group piece and the alkylaminoarylcarbonyl compound, the coupler-timing group piece having the formula:

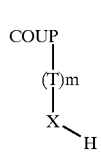

Formula II wherein

COUP is a photographic coupler residue capable of coupling with oxidized color developer to form a first dye;

T is a timing group;

m is an integer from 0 to 2; and

X is O, S, or N($R_1$) where $R_1$ is hydrogen or alkyl; and (3) making a methine dye via condensation reaction of the carbonyl portion of coupler-timing group-alkylaminoarylcarbonyl compound with active methylene portion of the rest of a dye molecule having the formula:

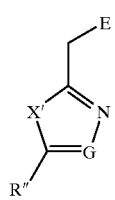

Formula III wherein

E is an electron withdrawing group;

X' is O, S, or N($R_2$) where $R_2$ is hydrogen or alkyl;

G is N or C($R_3$) where $R_3$ is hydrogen or a substituent;

R" is a substituent linked to the heterocycle by a carbon or nitrogen atom of the substituent, provided that R" and $R_3$ may be linked to form a ring and provided further that when R" and $R_3$ form a phenyl ring, Z' is hydrogen, G is C($R_3$), and X is O, the phenyl ring does not contain a substituent having a Hammett's sigma (para) value of 0.23 or more. The rest of embodiment of dye molecule is same as in U.S. Pat. No. 5,457,004.

It is intended that the term carbamyl compounds as used herein encompasses the closely related thocarbamyl; compounds.

The use of the intermediates of Formula I provides flexibility and simplicity in the preparation of high dye-yield couplers. Several small parts of couplers can be made separately and put together to build such a complex coupler molecule. All the reactions involved in making and using the intermediates are simple and efficient, and give high yield of products, so that the cost of manufacturing the couplers can be greatly reduced. The efficient reactions allow to combine intermediate steps reducing the cost further and generating less wastes.

DETAILED DESCRIPTION OF THE INVENTION

As described in the preceding summary of the invention, the present invention relates to alkylaminoarylcarbonyl compounds, intermediates for the preparation of high dye-yield couplers, process of making and using them, the high dye-yield couplers having the formula:

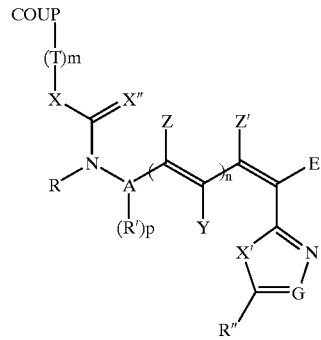

Formula IV wherein X" is O or S. It means that the present invention provides noble intermediates of Formula I which are parts of methine dye molecules, a noble process of making them and attaching them to a parent coupler-timing group piece of Formula II first and forming the methine dye last with the rest of methine dye molecule of Formula III to build high dye-yield couplers of Formula IV.

In the intermediates of Formula I, R is a substituted or unsubstituted alkyl group, such as alkyl containing 1 to 42, typically 1 to 22 carbon atoms. The R substituent can be any substituent that does not adversely affect the coupler. Representative substituted alkyls include branched alkyls, cyclic alkyls, arylalkyls, hetararylalkyls, or alkyls substituted with halogens or inert hetero atoms. Preferred branched alkyls are isopropyl, 2-methylpropyl, sec-butyl, 3-methylbutyl, 3-methyl-2-butyl, 3,3-dimethyl-2-butyl, 4-methyl-3-buten-2-yl, 2-pentyl, 3-pentyl, 4-methy-2-pentyl, 2-hexyl, 3-hexyl, 5-methyl-2-hexyl, 2-heptyl, 3-heptyl, 4-heptyl, 2-octyl, 5-nonyl, 2-undecyl, and the like. Preferred cyclic alkyls are cyclopropyl, cyclobutyl, cyclopentyl, cyclohexyl, 2-methylcyclohexyl, 4-methylcyclohexyl, 4-t-butylcyclohexyl, cycloheptyl, cyclooctyl, cyclononyl, cyclodecyl, cycloundecyl, cyclododecyl, and the like. Preferred arylalkyls are benzyl, 4-acet-amidobenzyl, 4-bromobenzyl, 4-butoxybenzyl, 4-butylbenzyl, 2-chlorobenzyl, 4-chlorobenzyl, 4-cyanobenzyl, 2,5-dimethoxybenzyl, 4-dimethylaminobenzyl, 4-ethylbenzyl, 2-methoxybenzyl, 4-methoxybenzyl, 4-methylbenzyl, 2-nitrobenzyl, 3-nitrobenzyl, 4-nitrobenzyl, 4-octylbenzyl, 3,4,5-trimethoxybenzyl, 1-naphthylmethyl-, 9-anathracylmethyl, 1-phenylethyl-, 2-phenylethyl, 1-phenylpropyl, 1-phenylbutyl, 2-methyl-1-phenylpropyl, 3-methyl-1-phenylbutyl, 1-phenyloctyl, 1-(4'-bromophenyl)

ethyl, 1-(4'-chlorophenyl)ethyl, 1-(2',4'-dichlorophenyl) ethyl, 1-(3',4'-dimethoxyphenyl)ethyl, 1-(2',5'-dimethylphenyl)-ethyl, 1-(4'-methoxyphenyl)ethyl, 1-(4'-methylphenyl)ethyl, 1-(1-naphthyl)ethyl, 1-(2-naphthyl) ethyl, and the like. Preferred heteroarylalkyls are 2-furylmethyl, 2-pyrrolemethyl, 2-pyridylmethyl, 2-thienylmethyl, 1-(2-furyl)ethyl, 1-(3-pyridyl)ethyl, 1-(4-pyridyl)-ethyl, 1-(2-thienyl)ethyl, and the like. Preferred alkyls substituted with halogens or inert hetero atoms include 1-chloro-2-propyl, 2-chloro-1-phenylethyl, 2-bromo-1-phenylethyl, 2-bromo-1-(4'-nitrophenyl)ethyl, 2-bromo-2-phenyl-1-phenylethyl, 1-methoxy-2-propyl, 1-methylmercapto-2-propyl, 1-dimethylamino-2-propyl, 2-methoxy-1-phenylethyl, 2-methylmercapto-1-phenylethyl, 2-dimethylamino-1-phenylethyl, 2-methoxy-1-(4'-nitro-phenyl)ethyl, 2-methylmercapto-1-(4'-nitrophenyl) ethyl, 2-dimethylamino-1-(4'-nitrophenyl)ethyl, 2-methoxy-2-phenyl-1-phenylethyl, and the like.

A is a substituted or unsubstituted aryl (including heteroaryl) ring containing up to three optional substituents R'. Suitably, A is a phenyl, naphthyl, or thiazole ring. Each R' is independently a substituted or unsubstituted alkyl group which may form a ring with Z or Z' when n=0, and p is an integer from 0 to 3. One or more R' substituents may be present which preferably include alkyl groups of from 1 to 5 carbon atoms such as methyl, ethyl, propyl, or isopropyl.

Each Z, Y, and Z' is independently hydrogen or a substituent. Preferred Z substituents are substituted or unsubstituted alkyl groups which may form a ring with R'. Y substituents preferably include alkyl groups of from 1 to 5 carbon atoms such as methyl, ethyl, propyl, or isopropyl. Preferred Z' substituents are also substituted or unsubstituted alkyl groups which may form a ring with R' when n=0.

n, which represents the number of conjugated vinyl groups and affects the hue of the dye, is 0, 1, or 2.

The common intermediates of the invention, alkylaminoarylcarbonyl compounds, can be synthesized in a number of ways. However, all known synthetic methods are not practical for a branched alkyl substituted aminoarylcarbonyl compound. A preferred synthetic route to the common intermediate, which is a part of this invention, involves blocking the carbonyl function of aminoarylcarbonyl compounds (R=H in the Formula I) via condensation with an active methylene compound as shown in the following scheme:

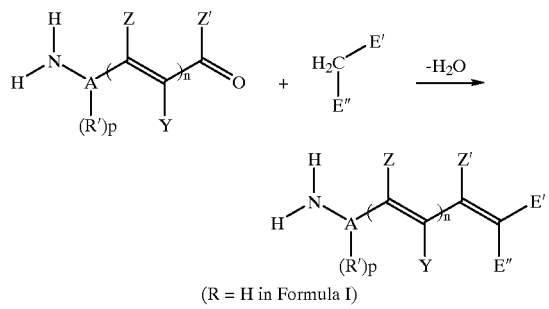

(R = H in Formula I)

Each E' and E" in the active methylene compound is independently an electron withdrawing group. The active methylene compound is used as a blocking group and will be removed later on. Therefore, the smaller and less expensive is the better. However, it should not be affected in the subsequent step. Suitable examples are cyano acetic acid, methyl or ethyl cyanoacetate, malononitrile, malonic acid, and dimethyl or diethyl malonate.

The starting aminoarylcompounds are readily available from nitroarenes by oxidation of alkyl groups accompanying the so-called Zinin reduction with aqueous alcoholic sodium polysulfide. The aminoarylcompounds are usually unstable because of self-condensation, so that it is used directly, without isolation, in the next blocking reaction.

The condensation reaction is well-known in literature. It is preferably done by azeotropic removal of water formed in the reaction which proceeds smoothly in the presence of a catalyst such as ammonium acetate and piperidine/acetic acid.

Alkylation of the blocked aminoarylcarbonyl compounds is easily done by reductive alkylation with alkyl, aralkyl, aryl, or heteroaryl carbonyl compounds corresponding to the desired R group in Formula I as shown in the following scheme:

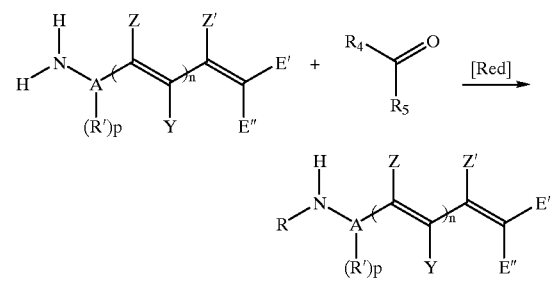

Each $R_4$ and $R_5$ is independently hydrogen, alkyl, aralkyl, aryl, or heteroaryl. $R_4$ and $R_5$ may form a carbocyclic or heterocyclic ring. The carbonyl compounds must be selected based on R group in Formula I.

The reductive alkylation of a primary amine with a carbonyl compound is well known reaction. It is preferrably done by catalytic hydrogenation or using a borane-amine complex. A number of practical borane-amine complexes are commercially available. Examples are borane-t-butylamine complex, borane-N,N-diethylaniline complex, borane-dimethylamine complex, and borane-pyridine complex.

Deblocking of blocked alkylaminoarylcarbonyl compounds to regenerate the carbonyl function and give the desired alkylaminocarbonyl compounds of Formula I is done by hydrolysis as shown in the following scheme:

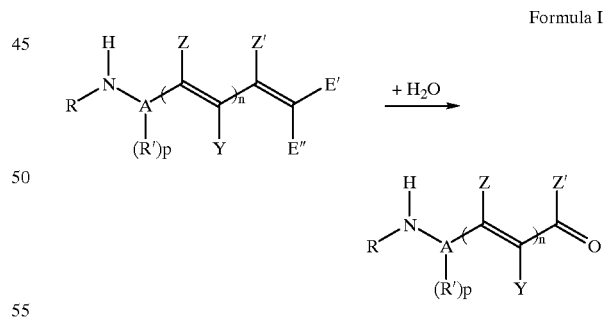

The hydrolysis can be done with an inorganic or organic base. Suitable inorganic bases are ammonium hydroxide, sodium hydroxide, potassium hydroxide, barium hydroxide, and calcium hydroxide. Suitable organic bases are triethylamine, tetramethyl-guanidine, 1,5-diazabicyclo[4,3,0]non-5-ene (DBN), 1,4-diazabicyclo[2,2,2]octane (Dabco), and 1,8-diazabicyclo[5,4,0]undec-7-ene (DBU).

EXAMPLE 1

Comparative Example

In a 500-ml flask, place 12.0 g (0.3 m) of sodium hydroxide pellets, 6.41 g (0.2 m) of sulfur powder, 18.0 g (0.075 m) of sodium sulfide nonahydrate, and 140 ml of distilled water. Heat the mixture with good stirring to about 70 C. to make an orange-red solution. In a 100-ml beaker, place 22.7 g (0.15 m) of 4-nitro-o-xylene, 2.4 g (5 mole %) of tetrabutlammonium bromide and 30 ml of isopropyl alcohol. Warm it to 50 C. with occasional stirring to make a clear pale-yellow solution. Add the solution in the beaker to the mixture in the 500-ml flask and use 10 ml of isopropyl alcohol to rinse the beaker and add to the reaction mixture. Heat the mixture with vigorous stirring under gentle reflux for 4.5 hours. Distill off isopropyl alcohol till approximately 50 ml of distillate is collected and pot/vapor temperature reaches to 100 C. Cool the reaction mixture to 20 C. Add 100 ml of propyl acetate and stir vigorously at room temperature for 5 minutes, and let layers settle. Separate off bottom water layer. Wash propyl acetate solution with 100 ml of water. Add 27 g (0.45 m) of acetyl anhydride slowly to propyl acetate solution containing 4-amino-2-methylbenzaldehyde. Stir the mixture at 40 C. for 1 hour. Add 100 ml of heptane and cool the mixture to room temperature. Stir slurry in a cold water bath for 1 hour. Collect solid, wash with 1:1 propyl acetate/heptane and dry to give 18.0 g (68%) of 4-acetylamino-2-methylbenzaldehyde.

In a 25-ml flask, place 1.77 g (0.01 m) of 4-acetylamino-2-methylbenzaldehyde and 5 ml of tetrahydrofuran. Add 2.24 g (0.02 m) of potassium t-butoxide and 4.47 g of cyclopentyl bromide. Stir the mixture at 40 C. for 24 hours. TLC of an aliquot of the reaction mixture shows that the reaction has not much proceeded, about 95% of starting material 4-acetylamino-2-methylbenzaldehyde remained unreacted, and a couple of new product spots appeared each as a faint and minor spot.

In separate experiments, alkylation of 4-acetylamino-2-methylbenzaldehyde with other base such as potassium carbonate, triethylamine, or DBU, and cyclopentylbromide or cyclopentyl tosylate gave similar results.

EXAMPLE 2 and 3

Examples of the Invention

The following schemes show two representative common intermediate examples, 4-cyclopentylamino-2-methylbenzaldehyde (Example 2) and 4-isopropylamnio-2-methylbenzaldehyde (Example 3), and illustrate the method of making them in accordance with the invention.

EXAMPLE 2

4-Cyclopentylamnio-2-methylbenzaldehyde

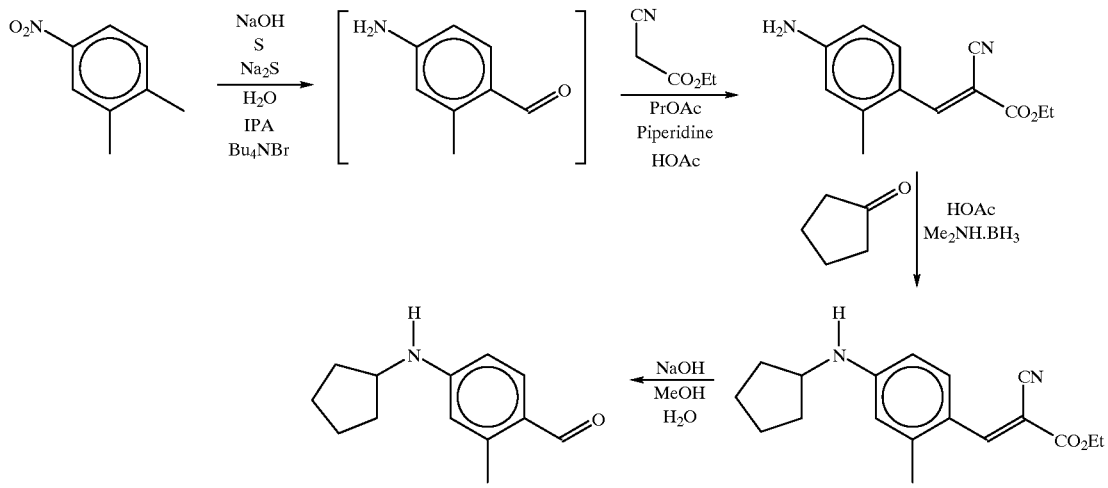

EXAMPLE 3

4-Isopropylamino-2-methlbenzaldehyde

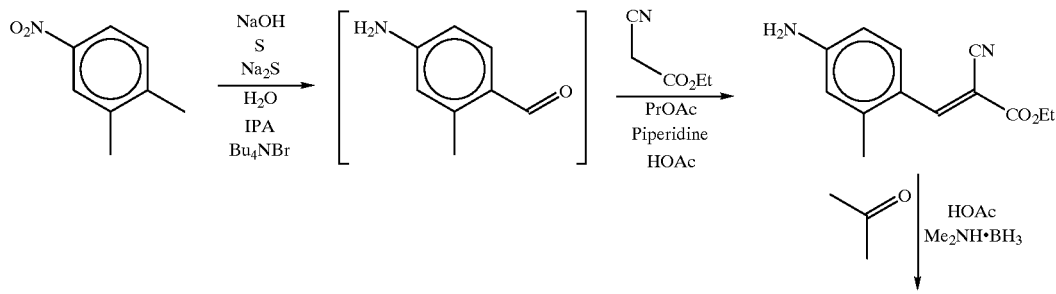

-continued

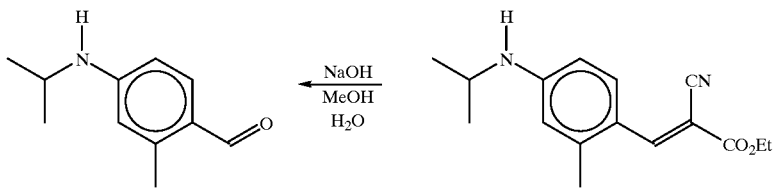

The following are typical synthetic procedures to make the common intermediates of the invention.

Synthesis of Example 2

In a 2-l flask, place 48.0 g (1.2 m) of sodium hydroxide pellets, 25.65 g (0.8 m) of sulfur powder, 72.0 g (0.3 m) of sodium sulfide nonahydrate, and 640 ml of distilled water. Heat the mixture with good stirring to about 70 C. to make an orange-red solution. In a 400-ml beaker, place 90.7 g (0.6 m) of 4-nitro-o-xylene, 9.6 g (0.03 m) of tetrabutylammonium bromide and 120 ml of isopropyl alcohol. Warm it to 50 C. with occasional stirring to make a clear pale-yellow solution. Add the solution in the beaker to the mixture in the 2-l flask and use 40 ml of isopropyl alcohol to rinse the beaker and add to the reaction mixture. Heat the mixture with vigorous stirring under gentle reflux (pot temperature 83 C.) for 4.5 hours. Distill off isopropyl alcohol till approximately 200 ml of distillate is collected and pot/vapor temperature reaches to 100 C. Cool the reaction mixture to 20 C. Add 400 ml of propyl acetate and stir vigorously at room temperature for 5 minutes, and let layers settle. Separate off bottom water layer. Add 400 ml of cold water and stir vigorously at room temperature for 5 minutes, and let layers settle. Separate bottom water layer. The propyl acetate solution contains 4-amino-2-methylbenzaldehyde intermediates. Add 61.1 g (0.54 m) of ethyl cyanoacetate, 1.6 g of piperidine, and 4.8 g of acetic acid. Stir the reaction mixture at room temperature for 30 min and then distill off propyl acetate under aspirator vacuum at pot/vapor temperature of 35–40 C. till no distillate comes off. Distillate comes out as an azeotropic mixture of propyl acetate and water with excess of propyl acetate. Add 120 ml of propyl acetate with gentle stirring while cooling to room temperature to get a fine yellow slurry. Add 300 ml of isopropyl ether slowly with a little faster stirring. Stir the product mixture for 20 minutes and let it stand at room temperature for 1 hour. Collect product, wash isopropyl ether, and dry to give 100.5 g (72.7%) of blocked aminobenzaldehyde intermediate.

In a 1-l flask, place 92.11 g (0.4 m) of the blocked aminobenzaldehyde, 250 ml of acetic acid and 67.3 g (0.8 m) of cyclopentanone. Heat the mixture to 40 C. Add 23.57 g (0.4 m) of borane-dimethylamine complex slowly keeping the temperature at 60 C. Stir the mixture at 60–65 C. for 1 hour, and cool to room temperature. Add 375 ml of water and stir for 15 minutes. Collect solids, wash with water, and deliquor as much as possible. In a 1-l flask, place the wet intermediate, 200 ml of methanol, and 120 g of 50% NaOH solution. Heat the mixture under reflux for 1 hour. Add 220 ml of hot water and distill off methanol till approximately 240 ml of distillate is collected and pot temperature reaches close to 100 C. Heat the mixture under reflux for 1 hour, and then cool to room temperature. Add 300 ml of propyl acetate, stir for 5 minutes, and let layers settle. Separate bottom water layer. Wash the propyl acetate solution with 200 ml of brine. Dry over magnesium sulfate and distill propyl acetate under a reduced pressure to a red viscous oil. Add 300 ml of heptanes with vigorous stirring. Stir the resulting slurry at room temperature for 45 minutes. Collect product, wash with heptanes, and dry to give 65.1 g (80%) of 4-cyclopentylamino-2-methylbenzaldehyde as yellow solids.

Synthesis of Example 3

The blocked aminobenzaldehyde intermediate is made in the same way as in the Synthesis of Example 2 above.

In a 500-ml flask, place 46.05 g (0.2 m) of the blocked aminobenzaldehyde, 125 ml of acetic acid and 23.23 g (0.4 m) of acetone. Heat the mixture to 30 C. Add 11.78 g (0.2 m) of borane-dimethylamine complex slowly keeping the temperature below 50 C. Stir the mixture at 50 C. for 1 hour, and cool to room temperature. Add 200 ml of water and stir for 15 minutes. Collect solids, wash with water, and deliquor as much as possible. In a 500-ml flask, place the wet intermediate, 100 ml of methanol, and 60 g of 50% NaOH solution. Heat the mixture under reflux for 1 hour. Add 120 ml of hot water and distill off methanol till approximately 120 ml of distillate is collected and pot temperature reaches close to 100 C. Heat the mixture under reflux for 1 hour, and then cool to room temperature. Add 150 ml of propyl acetate, stir for 5 minutes, and let layers settle. Separate bottom water layer. Wash the propyl acetate solution with 100 ml of brine. Dry over magnesium sulfate and distill propyl acetate under a reduced pressure to a red viscous oil. Add 150 ml of heptanes with vigorous stirring. Stir the resulting slurry at room temperature for 45 minutes. Collect product, wash with heptanes, and dry to give 28.35 g (80%) of 4-isopropylamino-2-methylbenzaldehyde as yellow solids.

In order to attach the common intermediates of the invention, alkylaminoarylcarb-onyl compounds, to the coupler-timing group piece of Formula II, they should be converted to carbamyl or thiocarbamyl chloride with phosgene or thiophosgene while protecting the carbonyl function in the form of a Schiff base prior to phosgenation. After the phosgenation of protected alkylaminoarylcarbonyl compounds, the protecting group can be readily removed by dilute acid hydrolysis. The following scheme illustrates the protection, phosgenation, and deprotection of the common intermediates of the invention:

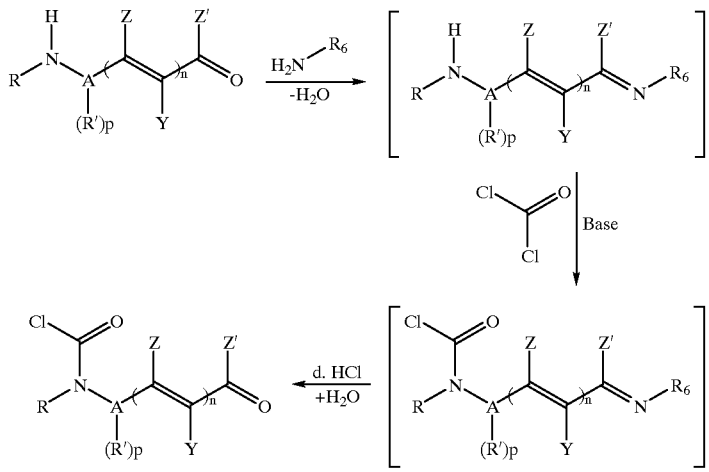

The Schiff base formation of a carbonyl compound with a primary amine is well known in literature. It is preferably done by azeotropic removal of water formed in the reaction which proceeds smoothly in the presence of an acid catalyst. Suitable primary amine examples for this Schiff base formation are t-butylamine, cyclohexylamine, and t-octylamine.

The Schiff base formed is not stable and is thus used directly, without isolation, in the phosgenation reaction. The phosgenation reaction is preferably done with a tertiary amine organic base such as triethylamine or 2,6-lutidine. The carbamyl chloride of the hindered amine is quite stable and survives in dilute acid hydrolysis of the Schiff base.

All the conversions are simple and efficient that they can be done in one pot giving a high quality and yield of product.

The thiocarbamyl chloride can be made in the same way as the carbamyl chloride using thiophosgene in place of phosgene.

The carbamyl or thiocarbamyl chloride of alkylaminoarylcarbonyl compounds can be readily and efficiently attached to a wide variety of coupler-timing group piece of Formula II. The following scheme illustrates the reaction:

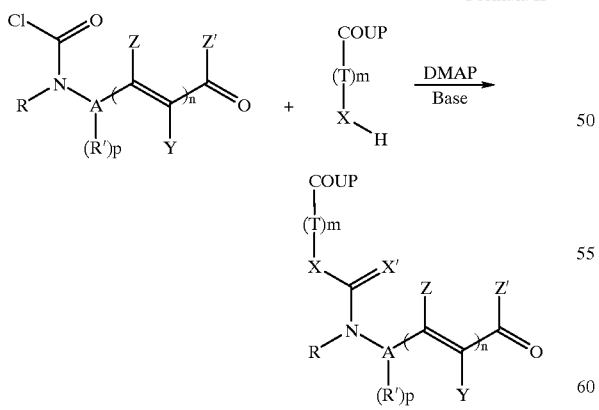

The reaction is preferably done with an acyl transfer agent such as 4-N,N-dimethylaminopyridine (DMAP) to activate the carbamyl or thiocarbamyl chloride and a strong organic base to ionize the proton of —X—H on coupler-timing group piece. Suitable strong organic bases for this reaction are triethylamine, 1,5-diazabicyclo[4,3,0]non-5-ene (DBN), 1,4-diazabicyclo[2,2,2]octane (Dabco), or 1,8-diazabicyclo[5,4,0]undec-7-ene (DBU).

In the coupler-timing group piece of Formula II, COUP is the parent portion of a coupler that is capable of coupling with oxidized developer to form a first dye. T is a timing group which, as indicated by the value range for m of from 0 to 2, may be absent or represent one or two such timing groups. Such couplers with or without timing groups are well known and described in U.S. Pat. No. 5,457,004 and references cited therein.

The methine dye formation can be done via condensation reaction of the carbonyl portion of coupler-timing group-alkylaminoarylcarbonyl compounds with active methylene

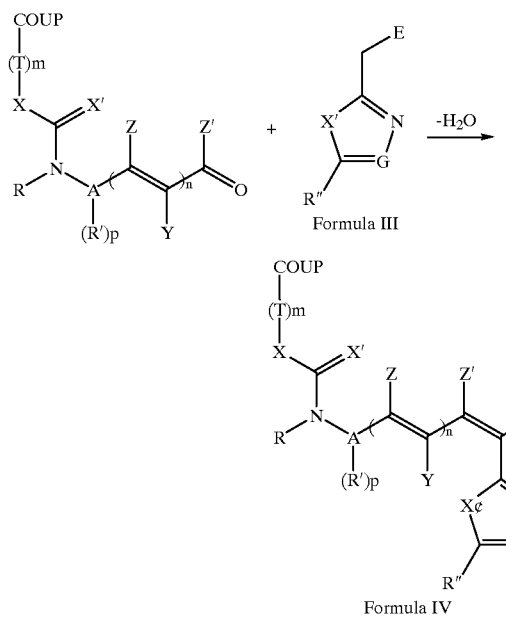

portion of the rest of dye molecules of the formula III as shown in the above scheme. This condensation is also preferably done by azeotropic removal of water formed in the reaction which proceeds smoothly in the presence of a catalyst such as piperidiene/acetic acid.

The following schemes show two examples of high dye-yield yellow couplers and illustrate the method of using the alkylaminoarylcarbonyl compounds, which is a part of the current invention. Coupler Example 1 illustrates the synthesis of a high-dye yield yellow coupler with a timing group using a common intermediate (Example 2) of the invention. Coupler Example 2 illustrates the synthesis of a high dye-yield yellow coupler without a timing group. The nitro group in the coupler of this example can be reduced to amine and attached to any kind of ballasting group to make a variety of different high dye-yield yellow couplers.

Coupler Example 1

A High Dye Yield Yellow Coupler With a Timing Group

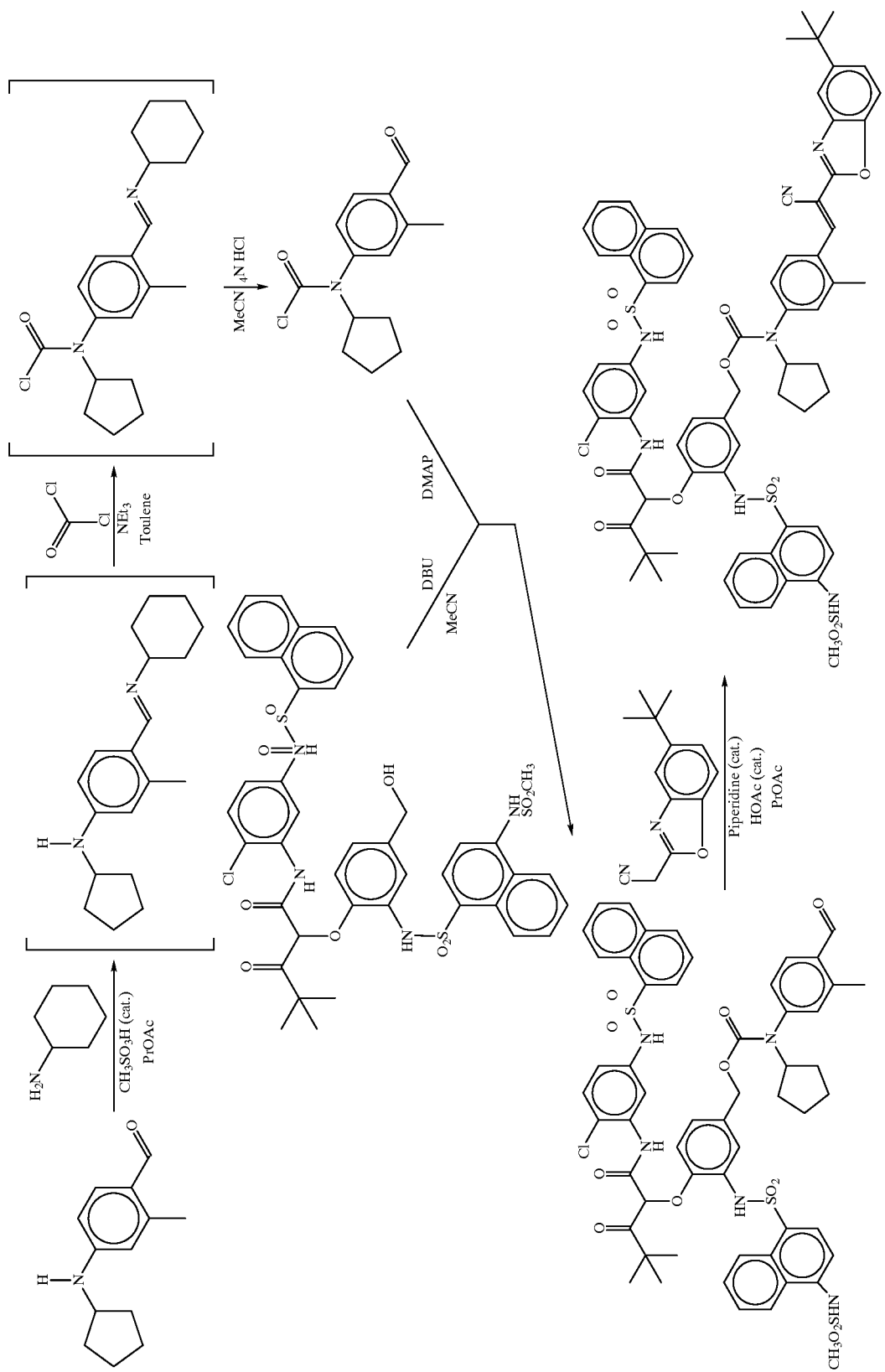

Coupler Example 2
A High Dye-Yield Yellow Coupler Without a Timing Group
The following are typical synthetic procedures to make the high-dye yield yellow couplers using the common intermediate, alkylaminoarylcarbonyl compounds, prepared by the method of the invention.
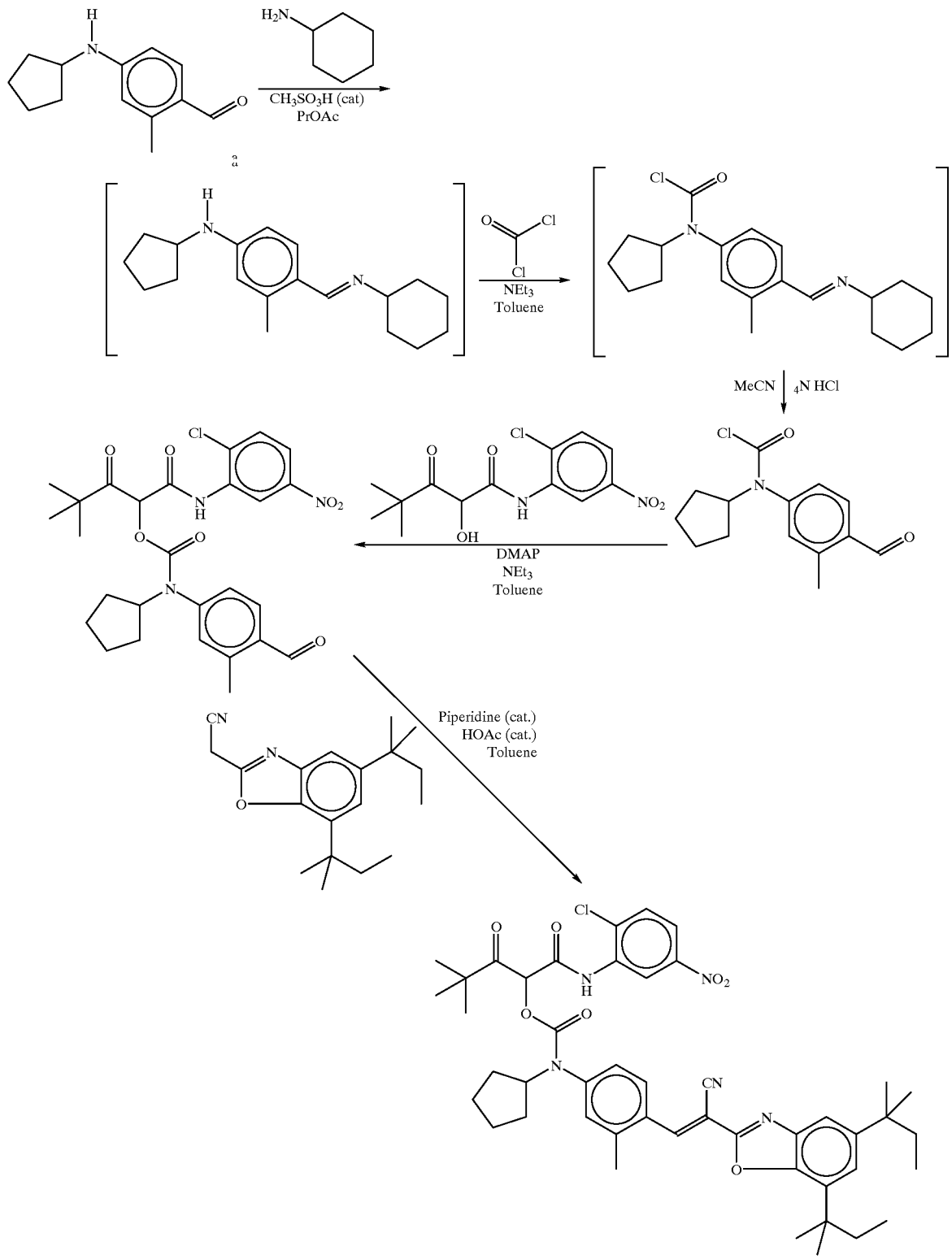

Coupler Example 1

In a 1-l flask, place 40.66 g (0.2 m) of 4-cyclopentylamino-2-methylbenzaldehyde (Example 1), 300 ml of propyl acetate, and 20.83 g (0.21 m) of cyclohexylamine. Stir the mixture to a solution. Add 1.0 g of methanesulfonic acid. Heat the mixture under reflux collecting water formed during the reaction. With a vigorous reflux, theoretical amount of water (3.6 ml) is collected in a Dean-Stark trap within an hour. Keep refluxing for additional 30 minutes and then distill off about 50 ml of propyl acetate at the end of refluxing time to make sure that Schiff base formation is complete. Cool the mixture to room temperature and then 0–5 C. in an ice bath. Add 35.4 g (0.35 m) of triethylamine and 160 ml (0.3 m) of 20% phosgene in toluene (d 0.935) from a dropping funnel over 20 min keeping the temperature at or below 20 C. Stir the mixture at room temperature for 1.5 hours. Degas and distill solvents under a reduced pressure keeping the pot temperature at 30–35 C. till no distillate comes off and a viscous oil left in the flask. Add 350 ml of acetonitrile and stir to dissolve the oil. Add 200 ml of 4N HCl and stir the mixture at room temperature for 2 hours. Add 200 ml of isopropyl ether and 200 ml of water (or more to fill-up to capacity of flask). Separate bottom water layer and wash upper organic layer with 250 ml of 1N HCl twice. Dry over magnesium sulfate and distill off solvent under a reduced pressure to give 48.1 g (90.5%) of light brown oil. This oil can be used as it is in the next step. To isolate pure carbamyl chloride, dissolve the oil in 100 ml of isopropyl ether and evaporate the solvent with no heat till product crystallizes and the mixture become a thick slurry. Let the mixture stand at 0–5 C. in an ice bath for at least 2–3 hours to get maximum return. Collect product with help of 1:1 (v/v) isopropyl ether-heptanes, wash with same mixed solvents, and dry to give 39.4 g (74%) of carbamyl chloride of 4-cyclopentylamino-2-methylbenzaldehyde In a 1-l flask inerted with nitrogen, place 43.97 g (0.05 m) of coupler-timing group piece shown in the scheme of Example 3 and 200 ml of acetonitrile. Stir the mixture to a suspension with nitrogen bubbling. Add 33.5 g (0.22 m) of DBU as a steady stream. Exotherm to 30–35 C. and clear solution occurs. Cool the solution to room temperature.

Add 6.72 g (0.055 m) of DMAP and 14.62 g (0.055 m) of carbamyl chloride of 4-cyclo-pentylamino-2-methylbenzaldehyde in 6 equal portions in 5 hours with 1 hour interval between each addition. After the final addition, keep stirring the mixture at room temperature for additional 3 hours. Add 300 ml of 4N HCl and 350 ml of propyl acetate. Stir for a few minutes and let layers settle. Separate bottom water layer. Concentrate upper propyl acetate solution under a reduced pressure at a pot temperature of 50–60 C. to a thick oil or a solid gum. Remove the heat source. Add 270 ml of propyl acetate to the mixture with a good stirring and add approximately 4 g of Celite. Filter insolubles through a Celite pad and wash with 30 ml of propyl acetate. Add 40 g of silica gel to the filtrate and stir for 5 min. Filter off the silica gel and wash with 50 ml of propyl acetate. The filtrate contains a reasonably pure coupler-timing group-alkylaminoarylcarbonyl intermediate and can be used as it is in the next step.

Place the filtrate in the original 1-l flask. Add 10.71 g (0.05 m) of 5-t-butyl-2-cyanomethylbenzoxazole, 0.3 g of piperidine and 0.9 g of acetic acid. Stir the mixture at 60–65 C. for 1 hour and slowly distill under a reduced pressure at 50–55 C. pot temperature (60–65 C. bath temperature) collecting initially an water/propyl acetate azeotrope and the propyl acetate till approximately 1 ml of water and 150 ml of propyl acetate is collected over 2 hour period. Run a TLC to confirm the reaction complete. Add 100 ml of water, stir for a minutes and layers settle. Separate water layer off. Distill about 50 ml of propyl acetate under a reduced pressure at 50–55 C. pot temperature. Add 75 ml of isopropyl ether with a good stirring. Cool to room temperature and then to 0–3 C. in an ice bath. Add seeds and stir at 0–3 C. for 3 hours. Let the mixture stand at 0–3 C. in an ice bath overnight. Collect product, wash with 2:1 (v/v) mixture of propyl acetate-isopropyl ether till washings are colorless, and dry to give 45.7 g (70%) of the coupler of Example 3 as bright yellow solids.

Coupler Example 2

The carbamyl chloride 4-cyclopentylamino-2-methylbenzaldehyde is made in the same way as in the Synthesis of Coupler Example 1 above.

In a 1-l flask inerted with nitrogen, place 26.57 g (0.1 m) of the carbamyl chloride, 12.22 g (0.1 m) of DMAP, and 350 ml of toluene. Stir the mixture at room temperature for 5 minutes. Add 31.47 g (0.1 m) of N-2-chloro-5-nitrophenyl-4,4-dimethyl-2-hydroxy-1,3-dioxopentanamide and 12.14 g (0.12 m) of triethylamine. Stir the mixture at 30 C. for 2 hours. Run a TLC to confirm the reaction complete. Add 300 ml of 2 N HCl with vigorous stirring. Filter insolubles through a Celite pad and wash with 100 ml of toluene. Separate bottom water layer. Wash toluene solution twice with 300 ml of 2N HCl each and dry over magnesium sulfate. The toluene solution contains a reasonably pure coupler-alkylaminoarylcarbonyl compound and can be used as it is in the next step.

Place the toluene solution in the original 1-l flask and 29.84 g (0.1 m) of 2-cyanomethyl-5,7-di-t-pentylbenzoxazole. Add 0.6 g of piperidine and 1.8 g of acetic acid. Stir the mixture at 60–65 C. for 1 hour and slowly distill under a reduced pressure at 60–65 C. pot temperature (70–75 C. bath temperature) collecting initially an azeotrope of water-toluene and the toluene till approximately 1.8 ml of water and 150 ml of toluene is collected over 2 hour period. Run a TLC to confirm the reaction complete. Cool the reaction mixture to room temperature. Add 300 ml of 1N HCl, stir for a few minutes and layers settle. Separate water layer and distill toluene under a reduced pressure at 60–65 C. pot temperature till no distillate comes off. Add 250 ml of methanol and heat to boil to dissolve viscous. Cool the methanol solution to room temperature with stirring. Continue to stir the resulting slurry at 15 C. for 2 hours. Collect solid, wash with methanol, and dry to give 60.2 g (73%) of the coupler as yellow solids.

The invention has been described above with particular reference to preferred embodiments thereof. A skilled worker being aware of the above detailed description can make many modifications or substitutions without departing from the scope or spirit of this invention. The patents and other publications cited herein are incorporated by reference in their entirety.

What is claimed is:

1. A method of making an alkylaminoarylcarbonyl compound having Formula I:

Formula I

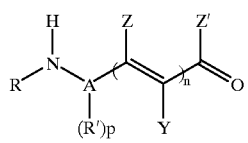

wherein

R is an alkyl, cycloalkyl or arylalkyl group;

A is a phenyl or naphthyl ring;

each R' is independently an alkyl group which may form a ring with Z or Z';

p is 0, 1, 2, or 3;

each Z, Z', and Y is independently hydrogen or an alkyl, cycloalkyl or arylalkyl group; and n is 0, 1, or 2;

comprising:

(a) blocking the carbonyl function of an aminoarylcarbonyl compound of the formula:

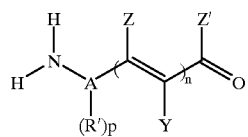

via condensation with an active methylene compound of formula:

wherein each E' and E" is independently a cyano, acetate, malonate, formic acid or formate group;

whereby there results a blocked aminoarylcarbonyl compound of formula:

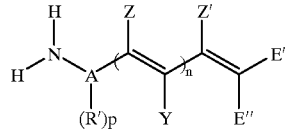

(b) alkylating this blocked amniocarbonyl compound via reductive alkylation with an alkyl or aryl carbonyl compound to give a blocked alkylaminoarylcarbonyl compound of formula:

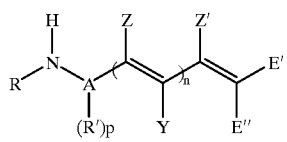

(c) deblocking of the blocked alkylaminoarylcarbonyl compound via base hydrolysis to regenerate the carbonyl function and give the desired alkylaminoarylcarbonyl compound.

2. The method of claim 1 wherein R is a straight chain or branched alkyl group with 1–20 carbon atoms.

3. The method of claim 2 wherein R is a methyl, ethyl, propyl, butyl, pentyl, hexyl, isopropyl, sec-butyl, 2-pentyl, 2-hexyl, cyclopropyl, cyclobutyl, cyclopentyl, cyclohexyl, 1-phenylethyl, 1-phenylpropyl, or 1-phenylbutyl group.

4. The method of claim 1 wherein one or more R' is an alkyl group having 1 to 5 carbon atoms.

5. The method of claim 4 wherein one or more R' is a methyl, ethyl, propyl, isopropyl, butyl, sec-butyl, t-butyl, pentyl, or neopentyl group.

6. The method of claim 1 wherein the active methylene compound used in step (a) is a cyano acetic acid, methyl cyanoacetate, ethyl cyanoacetate, malononitrile, malonic acid, dimethyl malonate, or diethyl malonate.

7. The method of claim 1 wherein the condensation reaction of step (a) is done in the presence of a catalyst which is a combination of weak base and weak acid.

8. The method of claim 7 wherein the catalyst is ammonium formate, ammonium acetate, ammonium propionate, pyrrolidine/formic acid, pyrrolidine/acetic acid, piperidine/formic acid, piperidine/acetic acid, morpholine/formic acid or morpholine/acetic acid.

9. The method of claim 7 wherein catalyst is present in the amount of 0.1–20 mole % based on the moles of aminoarylcarbonyl compound.

10. The method of claim 1 wherein step (b) is performed by hydrogenation using a catalyst, borohydride, or a borane-amine complex.

11. The method of claim 10 wherein hydrogenation is performed using a catalyst comprising nickel, cobalt, palladium, or platinum.

12. The method of claim 10 wherein the borohydride comprises lithium borohidride, sodium borohydride, potassium borohydride, or sodium cyanoborohydride.

13. The method of claim 10 using a borane amine complex that comprises borane-t-butylamine complex, borane-N,N-diethylaniline complex, borane-dimethylamine complex, or borane-pyridine complex.

14. The method of claim 1 wherein base hydrolysis of step (c) is performed in the presence of an inorganic base or an organic base.

15. The method of claim 14 wherein the inorganic base comprises ammonium hydroxide, sodium hydroxide, potassium hydroxide, barium hydroxide, or calcium hydroxide.

16. The method of claim 14 wherein the organic base comprises triethylamine, tetramethylguanidine, 1,5-diazabicyclo[4,3,0]non-5-ene, 1,4-diazabicyclo[2,2,2]octane, or 1,8-diazabicyclo[5,4,0]undec-7-ene.

* * * * *

UNITED STATES PATENT AND TRADEMARK OFFICE
CERTIFICATE OF CORRECTION

PATENT NO. : 6,124,503  
DATED : September 26, 2000  
INVENTOR(S) : Chang-Kyu Kim, Jared B. Mooberry, David Hoke, James J. Seifert It is certified that error appears in the above-identified patent and that said Letters Patent is hereby corrected as shown below:

Column 5,  
Line 65, insert -- (in which E' is cyano and E" is carboxy) -- after "cyano acetic acid".  
Line 66, insert -- (in which E' is cyano and E" is methoxycarbonyl or ethoxycarbonyl, respectively) -- after "methyl or ethyl cyanoacetate".

Claim 1,  
Amended to read as follows:

1. A method of making an alkylaminoarylcarbonyl compound having Formula I:

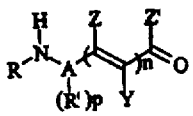

wherein  
    R is an alkyl, cycloalkyl or arylalkyl group;  
    A is a phenyl or naphthyl ring;  
    each R' is independently an alkyl group which may form a ring with Z or Z';  
    p is 0, 1, 2, or 3;  
    each Z, Z', and Y is independently hydrogen or an alkyl, cycloalkyl or arylalkyl group; and  
    n is 0, 1, or 2;  
comprising:  
    (a) blocking the carbonyl function of an aminoarylcarbonyl compound of the formula:

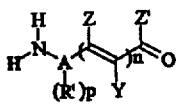

UNITED STATES PATENT AND TRADEMARK OFFICE
CERTIFICATE OF CORRECTION

PATENT NO. : 6,124,503
DATED : September 26, 2000
INVENTOR(S) : Chang-Kyu Kim, Jared B. Mooberry, David Hoke, James J. Seifert It is certified that error appears in the above-identified patent and that said Letters Patent is hereby corrected as shown below:

via condensation with an active methylene compound of formula:

wherein
  each E' and E" is independently a cyano, carboxyl, methoxycarbonyl, or ethoxycarbonyl group;
  whereby there results a blocked aminoarylcarbonyl compound of formula:

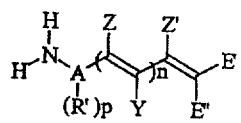

(b) alkylating this blocked aminocarbonyl compound via reductive alkylation with an alkyl or aryl (including heteroaryl) carbonyl compound to give a blocked alkylaminoarylcarbonyl compound of formula:

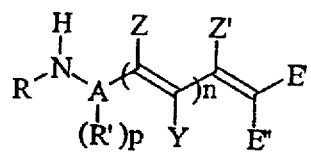

UNITED STATES PATENT AND TRADEMARK OFFICE
CERTIFICATE OF CORRECTION

PATENT NO. : 6,124,503
DATED : September 26, 2000
INVENTOR(S) : Chang-Kyu Kim, Jared B. Mooberry, David Hoke, James J. Seifert It is certified that error appears in the above-identified patent and that said Letters Patent is hereby corrected as shown below:

(c) deblocking of the blocked alkylaminoarylcarbonyl compound via base hydrolysis to regenerate the carbonyl function and give the desired alkylaminocarbonyl compound.

Signed and Sealed this

Eleventh Day of September, 2001

*Attest:*

*Attesting Officer*

NICHOLAS P. GODICI
*Acting Director of the United States Patent and Trademark Office*